US007045123B1

(12) United States Patent
Collmer et al.

(10) Patent No.: US 7,045,123 B1
(45) Date of Patent: May 16, 2006

(54) **DNA ENCODING *PSEUDOMONAS SYRINGAE* HYPERSENSITIVE RESPONSE ELICITOR AND ITS USE**

(75) Inventors: Alan Collmer, Ithaca, NY (US); Amy Charkowski, Madison, WI (US); James R. Alfano, Lincoln, NE (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/597,513

(22) Filed: Jun. 20, 2000

Related U.S. Application Data

(62) Division of application No. 09/120,817, filed on Jul. 22, 1998, now Pat. No. 6,172,184.

(60) Provisional application No. 60/055,107, filed on Aug. 6, 1997.

(51) Int. Cl.
*C12N 15/63* (2006.01)
*C12N 15/31* (2006.01)

(52) U.S. Cl. .................. 424/93.2; 536/23.7; 435/320.1

(58) Field of Classification Search ............... 536/23.7; 435/320.1, 418, 419, 252.3; 800/301, 305, 800/306, 317.1, 317.2, 309, 317.3, 310, 317.4, 800/311, 320.1, 312, 320.2, 313, 320.3, 314, 800/316, 317, 318, 320, 322, 323, 303.1, 800/323.2, 323.3, 279
See application file for complete search history.

(56) References Cited

U.S. PATENT DOCUMENTS

| | | | |
|---|---|---|---|
| 4,569,841 A | | 2/1986 | Liu |
| 4,597,972 A | | 7/1986 | Taylor |
| 4,601,842 A | | 7/1986 | Caple et al. |
| 4,740,593 A | | 4/1988 | Gonzalez et al. |
| 4,851,223 A | | 7/1989 | Sampson |
| 4,886,825 A | | 12/1989 | Ruess et al. |
| 4,931,581 A | | 6/1990 | Schurter et al. |
| 5,057,422 A | | 10/1991 | Bol et al. |
| 5,061,490 A | | 10/1991 | Paau et al. |
| 5,135,910 A | | 8/1992 | Blackburn et al. |
| 5,173,403 A | | 12/1992 | Tang |
| 5,217,950 A | | 6/1993 | Blackburn et al. |
| 5,243,038 A | | 9/1993 | Ferrari et al. |
| 5,244,658 A | | 9/1993 | Parke |
| 5,260,271 A | | 11/1993 | Blackburn et al. |
| 5,348,743 A | | 9/1994 | Ryals et al. |
| 5,494,684 A | | 2/1996 | Cohen |
| 5,523,311 A | | 6/1996 | Schurter et al. |
| 5,550,228 A | | 8/1996 | Godiard et al. |
| 5,552,527 A | | 9/1996 | Godiard et al. |
| 5,708,139 A | | 1/1998 | Collmer et al. |
| 5,850,015 A | * | 12/1998 | Bauer et al. |
| 6,001,959 A | | 12/1999 | Bauer et al. |

FOREIGN PATENT DOCUMENTS

| | | |
|---|---|---|
| EP | 0 612 848 A3 | 8/1994 |
| WO | WO 93/23532 | 11/1993 |
| WO | WO 94/10546 | 1/1994 |
| WO | WO 94/26782 | 11/1994 |
| WO | WO 95/19443 | 7/1995 |
| WO | WO 96/39802 | 12/1996 |
| WO | WO 98/15547 | 4/1998 |
| WO | WO 98/24297 | 6/1998 |
| WO | WO 98/32844 | 7/1998 |
| WO | WO 98/37752 | 9/1998 |
| WO | WO 98/54214 | 12/1998 |
| WO | WO 99/07206 | 2/1999 |
| WO | WO 99/07207 | 2/1999 |

OTHER PUBLICATIONS

Lazar et al. Transforming growth factor a: mutation of aspartic acid 47 and leucine 48 results in different biological activities Molecular and Cellular Biology, Mar. 1988 p. 1247-1252.*
Bowie et al. Deciphering the message in protein sequences: tolerence to amino acid substitutions Science vol. 247 .*
Broun et al. Catalytic plasticity of fatty acid modification enzymes underlying chemical diversity of plant lipids Science vol. 282 Nov. 13, 1998.*
Hill et al. Functional analysis of conserved histidines in ADP-Glucose pyrophosphorylase from *Escherichia coli* Biochemical and Biophysical Research Communications 244, 573-577 1998.*
He et al. Eliciation of plant hypersinsitive response by bacteria Plant Physiol. 1996 112-865-869.*
Keller et al. Pathogen-induced elicitin production in transgenic tobacco generates a hypersinsitive response and nonspecific disease resistance Plan Cell vol. 11 223-235 Feb. 1999.*
Bauer et al. New approaches to the development of trasgenic plants resistant to fire blight Acta Hort. 489, ISHS 1999 p. 301-304.*
Collmer et al Hrp Genes and Their Function Methods in Microbiology, vol. 27 p. 139-148.*

(Continued)

*Primary Examiner*—Anne Kubelik
(74) *Attorney, Agent, or Firm*—Nixon Peabody LLP

(57) ABSTRACT

The present invention is directed to an a isolated DNA molecule from *Pseudomonas syringae* that encodes a protein or polypeptide which elicits a hypersensitive response in plants. This isolated DNA molecule can used to impart disease resistance to plants, to enhance plant growth, and/or to control insects on plants. Plants or plant seeds transformed with a DNA molecule encoding a hypersensitive response elicitor protein or polypeptide can be provided, and the transgenic plants or plants resulting from the transgenic plant seeds are grown under conditions effective to impart disease resistance, to enhance plant growth, and/or to control insects on plants or plants grown from the plant seeds.

9 Claims, 3 Drawing Sheets

OTHER PUBLICATIONS

Tabakaki et al. Expression of the *Pseudomonas syringae* pv. *Phaseolicola hrpz* gene in transgenic tabacco and *Saccharomyces cerevisiae* pl392-396 1997.*
Sambrook et al, 1898, Molecular Cloning, A laboratory Manual, 2nd Ed. Cold Spring Harbor Laboratory press, p. 9.31-9.57.*
Guttman et al, 2002, Science 295: 1722-1726.*
Gopalan et al, 1996, Plant Dis. 80-604-610.*
Bonas, 1994, Trend Microbiol. 2:1-2.*
Bonas, 1994, Current Topics Microbiol Immunol. 192:79-98.*
Preston et al, 1995, MPMI 5:717-732.*
Sambrook et al, Molecular Cloning: A Laboratory Manual, $2^{nd}$ ed., Cold Spring Harbor Laboratory press, 1989, p. 9.47-9.57.*
Collmer et al., "*Erwinia chyrsanthemi* and *Pseudomonas syringae*: Plant Pathogens Trafficking in Extracellular Virulence Proteins," pp. 43-78.
Fredrick et al., "The WTS Water-Soaking Genes of *Erwinia stewartii* are Related to *hrp* Genes," Seventh International Symposium on Molecular Plant Microbe Interactions, Abstract No. 191 (Jun. 1994).
Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).
Preston et al., "The HrpZ Proteins of *Pseudomonas syringae* pvs. *syringae, glycinea,* and *tomato* are Encoded by an Operon Containing *Yersinia ysc* Homologs and Elicit the Hypersensitive Response in Tomato by not Soybean," *Mol. Plant-Microbe Interact*., 8(5):717-32 (1995).
Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).
Stryer, L., "Enzymes are Highly Specific," *Biochemistry*, San Francisco: W.H. Freeman and Company, p. 116 (1975).
Keen et al., "Inhibition of the Hypersensitive Reaction of Soybean Leaves to Incompatible *Pseudomonas* spp. by Blasticidin S, Streptomycin or Elevated Temperature," *Physiological Plant Pathology*, 18:325-37 (1981).
Lerner, R.A., "Tapping the Immunological Repertoire to Produce Antibodies of Predetermined Specificity," *Nature*, 299:592-96 (1982).
Staskawicz et al., "Cloned Avirulence Gene of *Pseudomonas syringae* pv. *glycinea* Determines Race-specific Incompatibility on *Glycine max* (L.) Merr.," *Proc. Nat. Acad. Sci. USA*, 81:6024-28 (1984).
Bauer et al., "*Erwinia chrysanthemi* $Harpin_{Ech}$: An Elicitor of the Hypersensitive Response that Contributes to Soft-Rot Pathogenesis," *MPMI*, 8(4):484-91 (1995).
Huang et al., "Characterization of the *hrp* Cluster from *Pseudomonas syringae* pv. *syring* and Tn*phoA* Tagging of Genes Encoding Exported or Membrane-Spanning Hrp Proteins," *Molec. Plant-Microbe Interact*., 4(5):469-76 (1991).
Huang et al., "The *Pseudomonas syringae* pv. *syringae* 61 *hrpH*Product, an Envelope Protein Required for Elicitation of the Hypersensitive Response in Plant," *J. Bacteriol*., 174(21):6878-85 (1992).
Bonas, U., "*hrp* Genes of Phytopathogenic Bacteria," *Current Topics in Microbio*., 192:79-98 (1994).
Arlat et al., "PopA1, A Protein Which Induces a Hypersensitivity-Like Response on Specific Protein *Petunia* Genotypes, is Secreted via the Hrp Pathway of *Pseudomonas solanacearum*," *The EMBO J.*, 13(3):543-53 (1994).
Kessmann et al., "Induction of Systemic Disease Resistance in Plants By Chemicals," *Ann. Rev. Phytopathol.*, 32:439-59 (1994).
Kelman, A., "The Relationship of Pathogenicity in *Pseudomonas solanacearum* To Colony Appearance on a Tetrazolium Medium," *Phytopathology*, 44:693-95 (1954).
Winstead et al., "Inoculation Techniques For Evaluating Resistance to *Pseudomonas solanacearum*," *Phytopathology*, 42:628-34 (1952).
Ahl et al., "Iron Bound-Siderophores, Cyanic Acid, and Antibiotics Involved in Suppression of *Thielaviopsis basiocola* by a *Pseudomonas fluorescens* Strain," *J. Phytopathology*, 116:121-34 (1986).
Anderson et al., "Response of Bean to Root Colonization with *Pseudomonas putida* in a Hydroponic System," *Phytopathology*, 75(9):992-95 (1985).
Gardner et al., "Growth Promotion and Inhibition by Antibiotic-Producing Fluorescent Pseudomonads on Citrus Roots," *Plant and Soil*, 77:103-13 (1984).
Kloepper, J.W., "Effert of Seed Piece Inoculation with Plant Growth-Promoting Rhizobacteria on Populations of *Erwinia carotovora* on Potato Roots and In Daughter Tubers," *Phytopathology*, 73(2):217-19 (1983).
Atkinson et al., "The Hypersensitive Reaction of Tobacco of *Pseudomonas syringae* pv. *pisi," Plant Physiol.*, 79:843-47 (1985).
Huynch et al., "Bacterial Blight of Soybean: Regulation of a Pathogen Gene Determining Host Cultivar Specificity," *Science*, 245:1374-77 (1986).
Kloepper et al., "Plant Growth-Promoting Rhizobacteria on Canola (Rapeseed)," *Plant Disease*, 72(1):42-6 (1988).
Kloepper et al., "Enhanced Plant Growth by Siderophores Produced by Plant-Growth-Promoting Rhizobacteria," *Nature*, 286:885-86 (1980).
Kloepper et al., "*Pseudomonas* Siderophores: A Mechanism Explaining Disease-Suppressive Soils," *Current Microbiology*, 4:317-20 (1980).
Kloepper et al., "Emergence-Promoting Rhizobacteria: Description and Implications for Agriculture," In: *Iron, Siderophores, and Plant Disease*, Swinborne (ed), Plenum, NY, 155-64 (1986).
Kloepper et al., "Relationships of in vitro Antibiosis of Plant Growth-Promoting Rhizobacteria to Plant Growth and the Displacement of Root Microflora," *Phytopathology*, 71(10):1020-24 (1981).
Kloepper et al., "Effects of Rhizosphere Colonization by Plant Growth-Promoting Rhizobacateria on Potato Development and Yield," *Phytopathology*, 70(11):1078-82 (1980).
Koepper et al., "Plant Growth Promotion Mediated by Rhizosphere Bacterial Colonizers," In: *The Rhizosphere and Plant Growth*, 315-32, Keister et al., (eds), pp. 315-26 (1991).
Lifshitz et al., "Growth Promotion of Canola (rapeseed) Seedlings by a Strain of *Pseudomonas putida* Under Gnotobiotic Conditions," Conditions *Microbiol.* 33:390-95 (1987).
Liu et al., "Induction of Systemic Resistance in Cucumber Against Bacterial Angular Leaf Spot by Plant-Growth-Promoting Rhizobacteria," *Phytopathology* 85(8):843-47 (1995).
Lopper et al., "Influence of Bacterial Sources of Indole-3-acetic Acid on Root Elongation of Sugar Beet," *Phytopathology*, 76(4):386-89 (1986).

Schroth et al., "Disease-Suppresive Soil and Root-Colonizing Bacteria," *Science*, 216:1376-81 (1982).
Stutz et al., "Naturally Occurring Fluorescent Pseudomonads Involved Suppression of Black Root Rot of Tobacco," *Phytopathology*, 76(2):181-85 (1986).
Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512-22 (1986).
Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425-29 (1987).
Wei et al., "Induction of Systemic Resistance on Cucumber to *Colletotrichum orbiculare* by Select Strains of Plant Growth-Promoting Rhizobacteria," *Phytopathology*, 81:15208-12 (1991).
Wei et al., "Induction of Systemic Resistance with Seed Treatment by PGPR Strains," pp. 191-194.
Weller, D.M., "Biological Control of Soilborne Plant Pathogens in the Rizosphere with Bacteria," *Ann. Rev. Phytopathol.*, 26:379-407 (1988).
Young et al., "PGPR: Is There a Relationship Between Plant Growth Regulators and the Stimulation of Plant Growth or Biological Activity?," pp. 182-186.
Wei et al., "Induced Systemic Resistance by Select Plant Growth-Promoting Rhizobacteria Against Bacterial Wilt of Cucumber and the Beetle Vectors," *Phytopathology*, 86:1154, Abstract No. 313 (1995).
Wieringa-Brants et al., Induced Resistance in Hypersensitive Tobacco Against Mosaic Virus by Injection of Intercellular Fluid from Tobacco Plants with Systemic Acquired Resistance, *Phytopathology*, 118:165-70 (1987).
Malamy et al., "Salicylic Acid: A Likely Endogenous Signal in the Resistance Response of Tobacco to Viral Infection," *Science*, 250:1002-04 (1990).
Dean et al., "Immunisation Against Disease: The Plant Fights Back," pp. 383-411.
Cameron et al., "Biologically Induced Systemic Acquired Resistance in *Arbidopisis thaliana*," *The Plant Journal*, 5(5):715-25 (1994).
Laby et al., "Structural and Functional Analysis of *Erwingia amylovora* Harpin, An Elicitor of the Plant Hypersensitive Response," *Phytopathology*, 84:345 (1994).
Van Gijsegem et al., "Evolutionary Conservation of Pathogenicity Determinants Among Plant and Animal Pathogenic Bacteria," *Trends Micorbiol.*, 1:175-80 (1993).
Kamoun, et al., "Extracellular Protein Elicitors from *Phytophthora:* Host-Specificity and Induction of Resistance to Bacterial and Fungal Phytopathogens," *Molecular Plant-Microbe Interactions*, 6(1):15/25 (1993).
Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance" *The Plant Journal*, 8(4):551-60 (1995).
Collinge et al., "Plant Gene Expression in Response to Pathogens," *Plant Molecular Biology*, 9:389-410 (1987).
Shatzman et al., "Expression, Identification, and Characterization of Recombinant Gene Products in *Escherichia coli,*" *Methods in Enzymology*, 152:661-73 (1987).
Tenhaken, et al., "Function of the Oxidative Burst in Hypersensitive Disease Resistance," *Proc, Natl, Acad. Sci, USA*, 92:4158-63 (1995).
Bonnet, et al., "Induction de nécroses foliaires, de protéines b et de résistance dans les interactions tabac *Phytophthora,*" *Agronomie*, 6(9):829-37 (1986).
Gallitelli, et al., "Satellite-Mediated Protection of Tomato Against Cucumber Mosaic Virus: II. Field Test Under Natural Epidemic Conditions in Southern Italy," *Plant Disease*, 75(1):93-5 (1991).
Kang et al., "Control of Tomato Mosaic Disease by Interference of an Attenuated Virus," *Res. Rept. RDA* (*Hort.*), 27(1):17-26 (1985).
Montasser, et al., "Satellite-Mediated Protection of Tomato Against Cucumber Mosaic Virus: I. Greenhouse Experiments and Simulated Epidemic Conditions in the Field," *Plant Disease*, 75(1):86-92 (1991).3
Marks, R.J., "Varietal Resistance to Potato Cyst Nematode," *Agricultural Entomology*, pp. 63-67 (1979).
Walton, et al., "Host-Selective Toxins and Disease Specificity: Perspectives and Progress," *Annu. Rev. Phytopathol.*, 31:275-303 (1993).
Atkinson, M.M., "Molecular Mechanisms of Pathogen Recognition by Plants," *Advances in Plant Pathology*, 10:36-64 (1993).
Godiard, et al., "Differential Regulation in Tobacco Cell Suspensions of Genes Involved in Plant-Bacteria Interactions by Pathogen-Related Signals," *Plant Molecular Biology*, 17:409-13 (1991).
Ricci, et al., "Structure and Activity of Proteins from Pathogenic Fungi *Phytophthora* Eliciting Necrosis and Acquired Resistance in Tobacco," *Eur. J. Biochem.*, 183:555-63 (1989).
Lakhmatova, I.T., "Induction of Plant Resistance to Viral Diseases: Application of Vaccination," *Sel'skokhozyaistvennaya Biologiya, Biologiya* 3:39-51 (1991).
*Biologicheskii Zhurnal Armenii*, 31(3):305-09 (1978).
Lakhmatova, I.T., "Using Biologically Active Substances to Induced Plant Resistance to Viruses Immunization," *Sel'skokhozyaistvennaya Biologiya*, 3:13-22 (1992).
Shields, R., "Towards Insect-Resistant Plants," *Nature*, 328:12-13 (1987).
Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748-56 (1988).
Ricci, et al., "Differential Production of Parasiticein, an Elicitor of Necrosis and Resistance in Tobacco, by Isoates of *Phytophthora parasitica,*" *Plant Pathology*, 41:298-307 (1992).
Honée, et al., "Molecular Characterization of the Interaction Between the Fungal Pathogen *Cladosporium fulvum* and Tomato," *Advances in Molecular Genetics of Plant-Microbe Interactions*, 3:199-206 (1994).
Keller, et al., "Respones of Tobacco to Elicitins, Proteins From *Phytophthora Spp.* Eliciting Acquired Resistance," *Advances in Molecular Genetics of Plant-Microbe Interactions*, 3:327-32 (1994).
Keen, et al., "Bacteria Expressing Avirulence Gene D Produce a Specific Elicitor of the Soybean Hypersensitive Reaction," *Molecular Plant-Microbe Interactions*, 3(2):112-21 (1990).
Bauer, et al., "*Erwinia chrysanthemi hrp* Genes and Their Involvement in Soft Rot Pathogenesis and Elicitation of the Hypersensitive Response," *MPMI*, 7(5):573-81 (1994).

Schottens-Toma et al., "Purification and Primary Structure of a Necrosis-inducing Peptide from the Apoplastic Fluids of Tomato Infected with *Cladosporium fulvum* (syn. *Fulvia fulva*)," *Physiological and Molecular Plant Pathology*, 33:59-67 (1988).

Steinberger et al., "Creation and Complementation of Pathogenicity Mutants of *Erwinia amylovora," Molecular Plant-Microbe Interactions*, 1(3):135-44 (1988).

Beer et al., "The Hypersensitive Response is Elicited by *Escherichia coli* Containing a Cluster of Pathogenicity Genes from *Erwinia amylovora," Phytopathology*, 79(10):1156 (Abstract 169) (1989).

Haitt et al., "Production of Antibodies in Transgenic Plants," *Nature*, 342:76-8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230-34(1989).

Huang et al., "Isolation and Purification of a Factor from *Pseudomonas solanacearum* That Induces a Hypersensitive-like Response in Potato Cells," *Molecular Plant-Microbe Interactions*, 2(3):132-38 (1989).

James et al.,"Genetic Transformation of Apple (*Malus pumila* Mill.) Using a Disarmed Ti-binary Vector," *Plant Cell Reports*, 7:658-61 (1989).

Laby et al., "Cloning and Prelininary Characterization of an *hrp* Gene Cluster of *Erwinia amylovora" Phytopathology*, 79(10):1211 (Abstract 607) (1989).

Dow et al., "Extracellular Proteases from *Xanthomonas campestris* pv. *campestris*, the Black Rot Pathogen," *Applied and Environmental Microbiology*, 56(10):2994-98 (1990).

Walters et al., "Gene for Pathogenicity and Ability to Cause the Hypersensitive Reaction Cloned from *Erwinia amylovora," Physiological and Molecular Plant Pathology*, 36:509-21 (1990).

Wu et al., "Cloning, Genetic Organization, and Characterization of a Structural Gene Encoding Bacillopeptidace F from *Bacillus subtilis," The Journal of Biological Chemistry*, 265(12):6845-50 (1990).

Bauer et al., "Further Characterization of an *hrp* Gene Cluster of *Erwinia amylovora," Molecular Plant-Microbe Interactions*, 4(5):493-99 (1991).

Beer et al., "The *hrp* Gene Cluster of *Erwinia amylovora," Advances in Molecular Genetics of Plant-Microbe Interactions*, 1:53-60 (1991).

Benvenuto et al., "Phytoantibodies: A General Vector for the Expression of Immunoglobulin Domains in Transgenic Plants," *Plant Molecular Biology*, 17:865-74 (1991).

Milat et al., "Physiological and Structural Changes in Tobacco Leaves Treated with Cryptogein, a Proteinaceous Elicitor from *Phytophthora cryptogea," Phytopathology*, 81(11):1364-68 (1991).

Ruberti et al., "A Novel Class of Plant Proteins Containing a Homeodomain with a Closely Linked Leucine Zipper Motif," *The EMBO Journal*, 10(7):1787-91 (1991).

Quigley et al., "Necleotide Sequence and Expression of a Novel Glycine-Rich Gene from *Arabidopsis thaliana," Plant Molecular Biology*, 17:949-52 (1991).

van Kan et al., "Cloning and Characterization of cDNA of Avirulence Gene *avr9* of the Fungal Pathogen *Cladosporium fulvum*, Causal Agent of Tomato Leaf Mold," *Molecular Plant-Microbe Interactions*, 4(1):52-9 (1991).

Waldmann, T.A., "Monoclonal Antibodies in Diagnosis and Therapy," *Science*, 252:1657-62 (1991).

Willis et al., "*hrp* Genes of Phytopathogenic Bacteria," *Molecular Plant-Microbe Interactions*, 4:(2) 132-38 (1991).

Beer et al., "Are Harpins Universal Elicitors of the Hypersensitive Response of Phytopathogenic Bacteria?," *Advances in Molecular Genetics of Plant-Microbe Interactions*, 2:281-86 (1992).

Laby et al., "Hybridization and Functional Complementation of the *hrp* Gene Cluster from *Erwinia amylovora* Strain Ea321 with DNA of Other Bacteria," *Molecular Plant-Microbe Interactions*, 5(5):412-19 (1992).

Sandhu, "Protein Engineering of Antibodies," *Crit. Rev. in Biotech.*, 12(5 / 6):437-62 (1992).

Wei et al., "Harpin, Elicitor of the Hypersensitive Response Produced by the Plant Pathogen *Erwinia amylovora," Science*, 257:85-8 (1992).

He et al., "*Pseudomonas syringae* pv. *syringae* $Harpin_{Pss}$: A Protein that is Secreted via the Hrp Pathway and Elicits the Hypersensitive Response in Plants," *Cell*, 73:1255-66 (1993).

Bonas, U., "Bacterial Home Goal by Harpins," *Trends in Microbiology*, 2:1-2 (1994).

Boccara, et al., "Plant Defense Elicitor Protein Produced by *Erwinai chrysanthemi," Mechanisms of Plant Defense Responses*, p. 166 (1993).

Qui et al., "Treatment of Tomato Seed with Harpin Enhances Germination and Growth and Induces Resistance to *Ralstonia solanacearum," Phytopathology*, 87:6, S80 (1997).

Burr et al.., "Increased Potato Yields by Treatment of Seedpieces with Specific Strains of *Pseudomonas Fluorescens* and *P. putida," Phytopathology*, 68:1377-1383 (1978).

Ricci et al., "Proteinaceous Elicitors of Plant Defence Responses," B. Fritig eds., *Mechanisms of Plant Defense Responses*, Netherlands, pp. 121-130 (1993).

Keen et al., "Syringolide Elicitors Specified By Avirulence Gene D Alleles In *Pseudomonas syringae," Advances in Molecular Genetics of Plant-Microbe Interactions*, 3:41-48 (1994).

Klessig et al., "The Salicyclic Acid Signal In Plants," *Plant Molecular Biology*, 26:1439-1458 (1994).

Bogdanvoe et al., "Unified Nomenclature For Broadly Conserved *hrp* Genes of Phytopathogenic Bacteria," *Molecular Microbiology*, 20(3):681-683 (1996).

Bonnet et al., "Aquired Resistance Triggered By Elicitins In Tobacco and Other Plants," *European Journal of Plant Pathology*, 102:181-192 (1996).

Cui et al., "The RsmA⁻Mutants of *Erwinia carotovora* subsp. *carotovora* Strain Ecc71 Overexpress $hrpN_{Ecc}$ and Elicit a Hypersensitive Reaction-like Response in Tobacco Leaves," *Molecular Plant-Microbe Interactions*, 9(7):565-573 (1996).

Gopalan et al., "Bacterial Genes Involved in the Elicitation of Hypersensitive Response and Pathogenesis," *Plant Disease*, 80(6):604-610 (1996).

Hoffland et al., "Comparison of Systemic Resistance Induced by Avirulent and Nonpathogenic *Pseudomonas* Species," *Phytopathology*, 86(7):757-762 (1996).

Ryals et al., "Systemic Aquired Resistance," *The Plant Cell*, 8:1809-1819 (1996).

Wei et al., "Induced Systemic Resistance to Cucumber Diseases and Increased Plant Growth by Plant Growth-Promoting Rhizobacteria Under Field Conditions," *Phytopathology*, 86:221-224 (1996).
Wengelnik et al., "Expression and Localization of HrpA1, a Protein of *Xanthomonas campestris* pv. vesicatoria Essential for Pathogenicity and Induction of the Hypersensitive Reaction," *Journal of Bacteriology*, 178:1061-1069 (1996).
Inbar et al., "Elicitors of Plant Defensive Systems Reduce Insect Densities and Diseases Incidence," *Journal of Chemical Ecology*, 24(1):135-149 (1998).
Jin et al., "A Truncated Fragment of $Harpin_{Pss}$ Induces Systemic Resistance To *Xanthomonas campetris* pv. *oryzae* In Rice," *Physiological and Molecular Plant Pathology*, 51:243-257 (1997).
Linthorst et al., "Constitutive Expression of Pathogenesis-Related Proteins PR-1, GRP, and PR-S in Tobacco Has No Effect on Virus Infection," *The Plant Cell* 1:285-291 (1989).
Lorang et al., "Characterization of *avrE* from *Pseudomonas syringae* pv. Tomato: A *hrp*Linked Locus Consisting Of at Least Two Transcriptional Units," *MPMI* 8(1):49-57 (1995).
Alfano et al., "Analysis of the Role of the *Pseudomonas syringae* pv. *syringae* HrpZ Harpin in Elicitation of the Hypersensitive Response in Tobacco Using Functionally Non-Polar *hrpZ* Delection Mutations, Truncated HrpZ Fragments, and *hrmA* Mutations," *Molecular Microbiology*, 19(4):715-728 (1996).
Malamy et al., Salicylic Acid and Plant Disease Resistance, *The Plant Journal*, 2(5):643-654 (1992).
McGurl et al., "Structure, Expression, and Antisense Inhibition of the Systemin Precursor Gene," *Science*, 255:1570-1573 (1992).
Schulte et al., "Expression of the *Xanthomonas campestris* pv. Vesicatoria *hrp* Gene Cluster, Which Determines Pathogenicity and Hypersensitivity on Pepper and Tomato, Is Plant Inductible," *Journal of Bacteriology*, 174:815-823 (1992).
Wu et al., "Disease Resistance Conferred by Expression of a Gene Encoding $H_2$ $H_2$-Generating Glucose Oxidase in Transgenic Potato Plants," *The Plant Cell*, 7:1357-1368 (1995).
Yu, "Elicitins from *Phytophthora* and Basic Resistance in Tobacco," *Proc. Natl. Acad. Sci. USA*, 92:4088-4094 (1995).
Nissinen et al., "*Clavibacter michiganensis* Subsp. Sepedonicus Elicits a Hypersensitive Response in Tobacco and Secretes Hypersensitive Response-Inducing Protein," *Phyopathology*, 87:679-684 (1997) (Abstract only).
US 5,650,387, 07/1997, Wei et al. (withdrawn)

* cited by examiner

SEQUENCE LISTING

```
<160> NUMBER OF SEQ ID NOS: 13

<210> SEQ ID NO 1
<211> LENGTH: 1729
<212> TYPE: DNA
<213> ORGANISM: Pseudomonas syringae

<400> SEQUENCE: 1

tccacttcgc tgattttgaa attggcagat tcatagaaac gttcaggtgt ggaaatcagg     60

ctgagtgcgc agatttcgtt gataagggtg tggtactggt cattgttggt catttcaagg    120

cctctgagtg cggtgcggag caataccagt cttcctgctg gcgtgtgcac actgagtcgc    180

aggcataggc atttcagttc cttgcgttgg ttgggcatat aaaaaaagga acttttaaaa    240

acagtgcaat gagatgccgg caaaacggga accggtcgct gcgctttgcc actcacttcg    300

agcaagctca accccaaaca tccacatccc tatcgaacgg acagcgatac ggccacttgc    360

tctggtaaac cctggagctg gcgtcggtcc aattgcccac ttagcgaggt aacgcagcat    420

gagcatcggc atcacacccc ggccgcaaca gaccaccacg ccactcgatt tttcggcgct    480

aagcggcaag agtcctcaac caaacacgtt cggcgagcag aacactcagc aagcgatcga    540

cccgagtgca ctgttgttcg gcagcgacac acagaaagac gtcaacttcg gcacgcccga    600

cagcaccgtc cagaatccgc aggacgccag caagcccaac gacagccagt ccaacatcgc    660

taaattgatc agtgcattga tcatgtcgtt gctgcagatg ctcaccaact ccaataaaaa    720

gcaggacacc aatcaggaac agcctgatag ccaggctcct ttccagaaca acggcgggct    780
```

-continued

```
cggtacaccg tcggccgata gcgggggcgg cggtacaccg gatgcgacag gtggcggcgg    840

cggtgatacg ccaagcgcaa caggcggtgg cggcggtgat actccgaccg caacaggcgg    900

tggcggcagc ggtggcggcg gcacacccac tgcaacaggt ggcggcagcg gtggcacacc    960

cactgcaaca ggcggtggcg agggtggcgt aacaccgcaa atcactccgc agttggccaa   1020

ccctaaccgt acctcaggta ctggctcggt gtcggacacc gcaggttcta ccgagcaagc   1080

cggcaagatc aatgtggtga aagacaccat caaggtcggc gctggcgaag tctttgacgg   1140

ccacggcgca accttcactg ccgacaaatc tatgggtaac ggagaccagg gcgaaaatca   1200

gaagcccatg ttcgagctgg ctgaaggcgc tacgttgaag aatgtgaacc tgggtgagaa   1260

cgaggtcgat ggcatccacg tgaaagccaa aaacgctcag gaagtcacca ttgacaacgt   1320

gcatgcccag aacgtcggtg aagacctgat tacggtcaaa ggcgagggag gcgcagcggt   1380

cactaatctg aacatcaaga acagcagtgc caaaggtgca gacgacaagg ttgtccagct   1440

caacgccaac actcacttga aatcgacaa cttcaaggcc gacgatttcg gcacgatggt   1500

tcgcaccaac ggtggcaagc agtttgatga catgagcatc gagctgaacg gcatcgaagc   1560

taaccacggc aagttcgccc tggtgaaaag cgacagtgac gatctgaagc tggcaacggg   1620

caacatcgcc atgaccgacg tcaaacacgc ctacgataaa acccaggcat cgacccaaca   1680

caccgagctt tgaatccaga caagtagctt gaaaaaaggg ggtggactc               1729
```

<210> SEQ ID NO 2
<211> LENGTH: 424
<212> TYPE: PRT
<213> ORGANISM: Pseudomonas syringae

<400> SEQUENCE: 2

```
Met Ser Ile Gly Ile Thr Pro Arg Pro Gln Gln Thr Thr Thr Pro Leu
  1               5                  10                  15

Asp Phe Ser Ala Leu Ser Gly Lys Ser Pro Gln Pro Asn Thr Phe Gly
             20                  25                  30

Glu Gln Asn Thr Gln Gln Ala Ile Asp Pro Ser Ala Leu Leu Phe Gly
         35                  40                  45

Ser Asp Thr Gln Lys Asp Val Asn Phe Gly Thr Pro Asp Ser Thr Val
     50                  55                  60

Gln Asn Pro Gln Asp Ala Ser Lys Pro Asn Asp Ser Gln Ser Asn Ile
 65                  70                  75                  80

Ala Lys Leu Ile Ser Ala Leu Ile Met Ser Leu Leu Gln Met Leu Thr
                 85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Gly Asp Thr
    130                 135                 140

Pro Ser Ala Thr Gly Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly Gly
                165                 170                 175

Ser Gly Gly Thr Pro Thr Ala Thr Gly Gly Gly Glu Gly Gly Val Thr
            180                 185                 190

Pro Gln Ile Thr Pro Gln Leu Ala Asn Pro Asn Arg Thr Ser Gly Thr
        195                 200                 205
```

-continued

```
Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
    290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
                325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
        355                 360                 365

Phe Asp Asp Met Ser Ile Glu Leu Asn Gly Ile Glu Ala Asn His Gly
    370                 375                 380

Lys Phe Ala Leu Val Lys Ser Asp Ser Asp Asp Leu Lys Leu Ala Thr
385                 390                 395                 400

Gly Asn Ile Ala Met Thr Asp Val Lys His Ala Tyr Asp Lys Thr Gln
                405                 410                 415

Ala Ser Thr Gln His Thr Glu Leu
            420


<210> SEQ ID NO 3
<211> LENGTH: 28
<212> TYPE: DNA
<213> ORGANISM: Pseudomonas syringae

<400> SEQUENCE: 3

atgaggatcc agcatcggca tcacaccc                                        28


<210> SEQ ID NO 4
<211> LENGTH: 28
<212> TYPE: DNA
<213> ORGANISM: Pseudomonas syringae

<400> SEQUENCE: 4

atgaaagctt aagctcggtg tgttgggt                                        28


<210> SEQ ID NO 5
<211> LENGTH: 28
<212> TYPE: DNA
<213> ORGANISM: Pseudomonas syringae

<400> SEQUENCE: 5

atgaaagctt gccaccgcct gttgcagt                                        28


<210> SEQ ID NO 6
<211> LENGTH: 28
<212> TYPE: DNA
<213> ORGANISM: Pseudomonas syringae

<400> SEQUENCE: 6
```

-continued

```
atgaggatcc gagggtggcg taacaccg                                         28


<210> SEQ ID NO 7
<211> LENGTH: 32
<212> TYPE: DNA
<213> ORGANISM: Pseudomonas syringae

<400> SEQUENCE: 7

ccatcgatgg tggtggcgat agctagactt gg                                    32


<210> SEQ ID NO 8
<211> LENGTH: 28
<212> TYPE: DNA
<213> ORGANISM: Pseudomonas syringae

<400> SEQUENCE: 8

ccatcgatgg tctcgtgatg gcaggttg                                         28


<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:  amino
      acids 121-128 of Pseudomonas syringae pv. tomato HrpZ

<400> SEQUENCE: 9

Gly Gly Gly Leu Ser Ser Asp Ala
  1               5


<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:  amino
      acids 234-244 of Pseudomonas syringae pv. tomato HrpZ

<400> SEQUENCE: 10

Gly Gly Gly Leu Gly Ser Pro Val Ser Asp Ser
  1               5                  10


<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:  amino
      acids 285-295 of Pseudomonas syringae pv. tomato HrpZ

<400> SEQUENCE: 11

Gly Gly Gly Leu Gly Thr Pro Val Asp Asn Ser
  1               5                  10


<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:  amino
      acids 211-220 of Pseudomonas syringae pv. syringae HrpZ

<400> SEQUENCE: 12

Gly Gly Leu Gly Thr Pro Ser Ser Phe Ser
  1               5                  10
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:  amino
      acids 265-270 of Pseudomonas syringae pv. syringae HrpZ

<400> SEQUENCE: 13

Gly Gly Leu Gly Thr Pro
  1               5
```

DNA ENCODING *PSEUDOMONAS SYRINGAE* HYPERSENSITIVE RESPONSE ELICITOR AND ITS USE

This application is a division of U.S. patent application Ser. No. 09/120,817, filed Jul. 22, 1998, and Now U.S. Pat. No. 6,172,184 entitled to benefit of U.S. Provisional Patent Application Ser. No. 60/055,107, filed Aug. 6, 1997.

This invention was developed with government funding under National Science Foundation Grant No. MCB 9631530. The U.S. Government may retain certain rights.

FIELD OF THE INVENTION

The present invention relates to a hypersensitive response elicitor from *Pseudomonas syringae* and its use.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response ("HR") is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199: 299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes*, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L. Dangl, ed. Springer-Verlag, Berlin (1994)). Several hrp genes encode components of a protein secretion pathway similar to one used by *Yersinia, Shigella*, and *Salmonella* spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae*, and *P. solanacearum*, hrp genes have been shown to control the production and secretion of glycine-rich, protein elicitors of the hypersensitive response (He, S. Y., et al. "*Pseudomonas Syringae* pv. *Syringae* Harpin$_{Pss}$: a Protein that is Secreted via the Hrp Pathway and Elicits the Hypersensitive Response in Plants," Cell 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum," EMBO J.* 13:543–553 (1994)).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora," Science* 257: 85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum," EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* Harpin$_{Ech}$: Soft-Rot Pathogenesis," *MPMI* 8(4): 484–91 (1995)); *Erwinia carotovora* (Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," *8th Int'l. Cong. Molec. Plant-Microb. Inter*. Jul. 14–19, 1996 and Ahmad, et. al., "Harpin is not Necessary for the Pathogenicity of *Erwinia stewartii* on Maize," *Ann. Mtg. Am. Phytopath. Soc. Jul.* 27–31, 1996); and *Pseudomonas syringae* pv. *syringae* (WO 94/26782 to Cornell Research Foundation, Inc.).

The present invention is a further advance in the effort to identify, clone, and sequence hypersensitive response elicitor proteins or polypeptides from plant pathogens.

SUMMARY OF THE INVENTION

The present invention is directed to an isolated protein or polypeptide which elicits a hypersensitive response in plants as well as an isolated DNA molecule which encodes the hypersensitive response eliciting protein or polypeptide.

The hypersensitive response eliciting protein or polypeptide can be used to impart disease resistance to plants, to enhance plant growth, and/or to control insects This involves applying the hypersensitive response elicitor protein or polypeptide in a non-infectious form to plants or plant seeds under conditions effective to impart disease resistance, to enhance plant growth, and/or to control insects on plants or plants grown from the plant seeds.

As an alternative to applying the hypersensitive response elicitor protein or polypeptide to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding a hypersensitive response elicitor protein or polypeptide and growing the plant under conditions effective to impart disease resistance, to enhance plant growth, and/or to control insects in the plants or plants grown from the plant seeds. Alternatively, a transgenic plant seed transformed with the DNA molecule encoding a hypersensitive response elicitor protein or polypeptide can be provided and planted in soil. A plant is then propagated under conditions effective to impart disease resistance, to enhance plant growth, and/or to control insects on plants or plants grown from the plant seeds.

BRIEF DESCRIPTION OF THE DRAWINGS

FIG. 2A shows a physical map of the DC3000 genome adjacent to the hrp gene cluster with open arrows denoting putative $\sigma^{54}$ promoters and filled arrows denoting putative HrpL-dependent promoters that control previously defined transcriptional units (Lorang, J. M., et al., *Mol. Plant-Microbe Interact.,* 8:49–57 (1995), which is hereby incorporated by reference). hrpR and hrpS encode regulatory proteins and are located at the right end of the hrp cluster. Numbers in boxes above the map give the percent identity of DC3000 DNA and colinearly arranged partial B728a DNA sequences. In FIG. 2B, the diagram of HrpW indicates the hypersensitive response elicitor-like and pectate lyase ("Pel")-like domains. The PCR subclone-generated $His_6$-tagged hypersensitive response elicitor domain fragment encompasses amino acids 1–186; the $His_6$-tagged Pel domain has amino acids 187–425. FIG. 2C shows the sequence of the region in the middle of HrpW that contains 6 glycine-rich repeats (see box) (aa 119–186 of SEQ ID NO: 2), with similar repeats in the HrpZ proteins from *P. syringae* pv. tomato ("Pto") (aa 121–128=SEQ ID NO: 9, aa 234–244=SEQ ID NO: 10, aa 285–295=SEQ ID NO: 11), and *P. syringae* pv. *syringae* ("Pss") (aa 211–220=SEQ ID NO: 12, aa 265–270=SEQ ID NO: 13) aligned below. Dashes were introduced where necessary to preserve alignment.

In FIG. 4A, $His_6$-tagged full-length HrpW and the two domain fragments were partially purified by Ni-NTA chromatography, separated by SDS-PAGE, and stained with Coomassie Blue R250. The arrow indicates the full-length HrpW, which is produced in very low amounts. Lanes: 1, Pel domain fragment; 2, hypersensitive response elicitor domain fragment; 3, HrpW. In FIG. 4B, the same HrpW derivatives were also visualized on immunoblots with anti-HrpW antibodies used in conjunction with the Western Light chemiluminescence assay. Lanes: 4, Pel domain fragment; 5, hypersensitive response elicitor domain fragment; 6, HrpW.

FIG. 5A, *P. syringae* pv. *syringae* 61 HrpZ (0.12 μg/ml); FIG. 5B, HrpW; FIG. 5C, harpin domain fragment of HrpW (0.22 μg/ml); FIG. 5D, HrpZ+lanthanum chloride; FIG. 5E, HrpW+ lanthanum chloride; FIG. 5F, Pel domain fragment of HrpW (1.40 μg/ml).

DETAILED DESCRIPTION OF THE INVENTION

Figure 1:
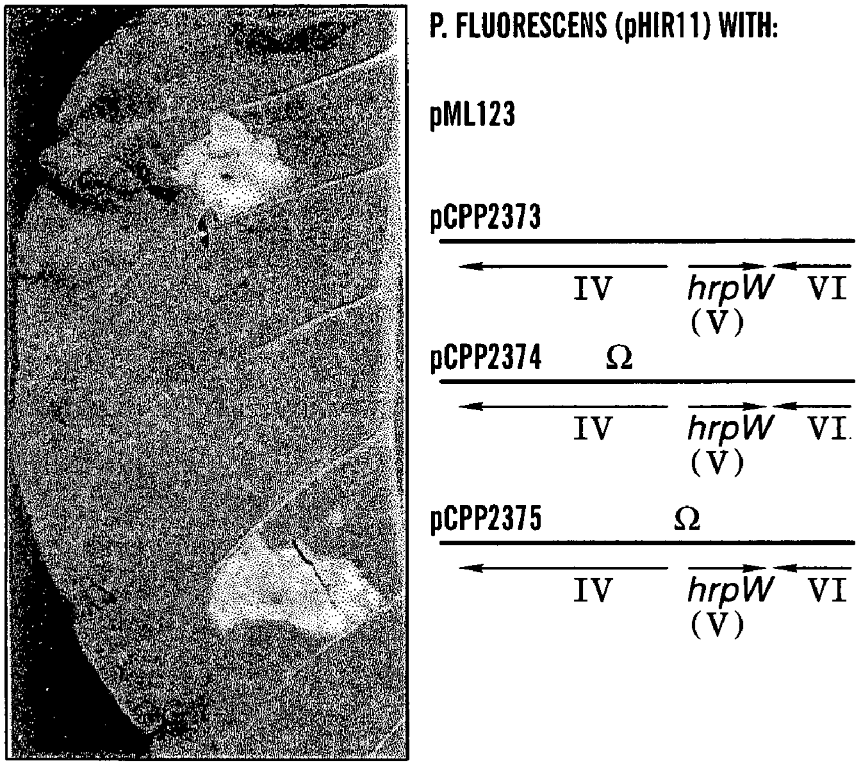
FIG. 1 shows the inhibition of the HR elicited in tobacco by *P. fluorescens*(pHIR11) by expression in trans of the *P. syringae* pv. tomato DC300 hrpW. Vector pML 123 derivatives carrying the hrpW region, two of which have Ω $Sp^r$ insertions at the indicated site, are shown at the left. The effects on a tobacco leaf of *P. fluorescens* cells carrying these constructs, 24 hr after inoculation at a concentration of $5\times10^8$ cells/ml, are shown at the right.

The present invention relates to an isolated DNA molecule having a nucleotide sequence of SEQ. ID. No. 1 as follows:

```
TCCACTTCGC TGATTTTGAA ATTGGCAGAT TCATAGAAAC GTTCAGGTGT GGAAATCAGG    60

CTGAGTGCGC AGATTTCGTT GATAAGGGTG TGGTACTGGT CATTGTTGGT CATTTCAAGG   120

CCTCTGAGTG CGGTGCGGAG CAATACCAGT CTTCCTGCTG GCGTGTGCAC ACTGAGTCGC   180

AGGCATAGGC ATTTCAGTTC CTTGCGTTGG TTGGGCATAT AAAAAAAGGA ACTTTTAAAA   240

ACAGTGCAAT GAGATGCCGG CAAAACGGGA ACCGGTCGCT GCGCTTTGCC ACTCACTTCG   300
```

-continued

```
AGCAAGCTCA ACCCCAAACA TCCACATCCC TATCGAACGG ACAGCGATAC GGCCACTTGC     360

TCTGGTAAAC CCTGGAGCTG GCGTCGGTCC AATTGCCCAC TTAGCGAGGT AACGCAGCAT     420

GAGCATCGGC ATCACACCCC GGCCGCAACA GACCACCACG CCACTCGATT TTTCGGCGCT     480

AAGCGGCAAG AGTCCTCAAC CAAACACGTT CGGCGAGCAG AACACTCAGC AAGCGATCGA     540

CCCGAGTGCA CTGTTGTTCG GCAGCGACAC ACAGAAAGAC GTCAACTTCG GCACGCCCGA     600

CAGCACCGTC CAGAATCCGC AGGACGCCAG CAAGCCCAAC GACAGCCAGT CCAACATCGC     660

TAAATTGATC AGTGCATTGA TCATGTCGTT GCTGCAGATG CTCACCAACT CCAATAAAAA     720

GCAGGACACC AATCAGGAAC AGCCTGATAG CCAGGCTCCT TTCCAGAACA ACGGCGGGCT     780

CGGTACACCG TCGGCCGATA GCGGGGGCGG CGGTACACCG GATGCGACAG GTGGCGGCGG     840

CGGTGATACG CCAAGCGCAA CAGGCGGTGG CGGCGGTGAT ACTCCGACCG CAACAGGCGG     900

TGGCGGCAGC GGTGGCGGCG GCACACCCAC TGCAACAGGT GGCGGCAGCG GTGGCACACC     960

CACTGCAACA GGCGGTGGCG AGGGTGGCGT AACACCGCAA ATCACTCCGC AGTTGGCCAA    1020

CCCTAACCGT ACCTCAGGTA CTGGCTCGGT GTCGGACACC GCAGGTTCTA CCGAGCAAGC    1080

CGGCAAGATC AATGTGGTGA AAGACACCAT CAAGGTCGGC GCTGGCGAAG TCTTTGACGG    1140

CCACGGCGCA ACCTTCACTG CCGACAAATC TATGGGTAAC GGAGACCAGG GCGAAAATCA    1200

GAAGCCCATG TTCGAGCTGG CTGAAGGCGC TACGTTGAAG AATGTGAACC TGGGTGAGAA    1260

CGAGGTCGAT GGCATCCACG TGAAAGCCAA AAACGCTCAG GAAGTCACCA TTGACAACGT    1320

GCATGCCCAG AACGTCGGTG AAGACCTGAT TACGGTCAAA GGCGAGGGAG GCGCAGCGGT    1380

CACTAATCTG AACATCAAGA ACAGCAGTGC CAAAGGTGCA GACGACAAGG TTGTCCAGCT    1440

CAACGCCAAC ACTCACTTGA AAATCGACAA CTTCAAGGCC GACGATTTCG GCACGATGGT    1500

TCGCACCAAC GGTGGCAAGC AGTTTGATGA CATGAGCATC GAGCTGAACG GCATCGAAGC    1560

TAACCACGGC AAGTTCGCCC TGGTGAAAAG CGACAGTGAC GATCTGAAGC TGGCAACGGG    1620

CAACATCGCC ATGACCGACG TCAAACACGC CTACGATAAA ACCCAGGCAT CGACCCAACA    1680

CACCGAGCTT TGAATCCAGA CAAGTAGCTT GAAAAAAGGG GGTGGACTC                1729
```

This DNA molecule is known as the hrpW gene. This isolated DNA molecule of the present invention encodes a protein or polypeptide which elicits a plant pathogen's hypersensitive response having an amino acid sequence of SEQ. ID. No. 2 as follows:

```
Met Ser Ile Gly Ile Thr Pro Arg Pro Gln Gln Thr Thr Thr Pro Leu
1               5                   10                  15

Asp Phe Ser Ala Leu Ser Gly Lys Ser Pro Gln Pro Asn Thr Phe Gly
            20                  25                  30

Glu Gln Asn Thr Gln Gln Ala Ile Asp Pro Ser Ala Leu Leu Phe Gly
        35                  40                  45

Ser Asp Thr Gln Lys Asp Val Asn Phe Gly Thr Pro Asp Ser Thr Val
    50                  55                  60

Gln Asn Pro Gln Asp Ala Ser Lys Pro Asn Asp Ser Gln Ser Asn Ile
65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125
```

-continued

```
Gly Gly Gly Gly Thr Pro Asp Ala Thr Gly Gly Gly Gly Gly Asp Thr
    130                 135                 140

Pro Ser Ala Thr Gly Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly Gly
                165                 170                 175

Ser Gly Gly Thr Pro Thr Ala Thr Gly Gly Gly Glu Gly Gly Val Thr
            180                 185                 190

Pro Gln Ile Thr Pro Gln Leu Ala Asn Pro Asn Arg Thr Ser Gly Thr
        195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
    290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
                325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
        355                 360                 365

Phe Asp Asp Met Ser Ile Glu Leu Asn Gly Ile Glu Ala Asn His Gly
    370                 375                 380

Lys Phe Ala Leu Val Lys Ser Asp Ser Asp Asp Leu Lys Leu Ala Thr
385                 390                 395                 400

Gly Asn Ile Ala Met Thr Asp Val Lys His Ala Tyr Asp Lys Thr Gln
                405                 410                 415

Ala Ser Thr Gln His Thr Glu Leu
            420
```

This protein or polypeptide is about 42.9 kDa.

Fragments of the above hypersensitive response elicitor polypeptide or protein are encompassed by the present invention.

Suitable fragments can be produced by several means. In the first, subclones of the gene encoding the elicitor protein of the present invention are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of SEQ. ID. No. 1 under stringent conditions. An example of suitable high stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μm g/ml *E. coli* DNA. However, any DNA molecules hybridizing to a DNA molecule comprising the nucleotide sequences of SEQ. ID. No. 1, under such stringent conditions must not be identical to the nucleic acids encoding the hypersensitive response elicitor proteins or polypeptides of *E. amylovora* (as disclosed by Wei, Z.-M., et al, "Harpin, Elicitor of the Hypersensitive Response Produced by the Plant Pathogen *Erwinia amylovora," Science* 257:85–88 (1992), which is hereby incorporated by reference), *Erwinia chrysanthemi* (as disclosed by Bauer, et. al., "*Erwinia* chrysanthemi Harpin$_{ECh}$: Soft-Rot Pathogenesis," *MPMI* 8(4): 484–91 (1995), which is hereby incorporated by reference), *Erwinia carotovora* (as disclosed by Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966), which is hereby incorporated by reference), *Erwinia stewartii* (as disclosed by Ahnmad, et. al., "Harpin is not Necessary for the Pathogenicity of *Erwinia stewartii* on Maize," 8*th Int'l. Cong. Molec. Plant-Microb. Inter*. Jul. 14–19, 1996 and Ahmad, et. al., "Harpin is not Necessary for the Pathogenicity of *Erwinia stewartii* on Maize," *Ann. Mtg. Am. Phytopath. Soc*. Jul. 27–31, 1996), which are hereby incorporated by reference), and *Pseudomonas syringae* pv. *syringae* (WO 94/26782 to Cornell Research Foundation, Inc., which is hereby incorporated by reference).

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins If necessary, the protein fraction may be further purified by HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/−or KS +/−(see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA.

This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, Ipp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance to plants, enhancing plant growth, and/or effecting insect control for plants. These methods involve applying a hypersensitive response elicitor polypeptide or protein in a non-infectious form to all or part of a plant or a plant seed under conditions where the polypeptide or protein contacts all or part of the cells of the plant or plant seed. Alternatively, the hypersensitive response elicitor protein or polypeptide can be applied to plants such that seeds recovered from such plants themselves are able to impart disease resistance in plants, to enhance plant growth, and/or to effect insect control.

As an alternative to applying a hypersensitive response elicitor polypeptide or protein to plants or plant seeds in order to impart disease resistance in plants, to effect plant growth, and/or to control insects on the plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to impart disease resistance to plants, to enhance plant growth, and/or to control insects. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to impart disease resistance to plants, to enhance plant growth; and/or to control insects.

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptide or protein of the present invention can be isolated from *Pseudomonas syringae* pv. tomato as described in the Examples infra. Preferably, however, the isolated hypersensitive response elicitor polypeptide or protein of the present invention is produced recombinantly and purified as described supra.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seed cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli*, which does not elicit a hypersensitive response in plants, can be transformed with genes encoding a hypersensitive response elicitor polypeptide or protein and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Pseudomonas syringae* pv. tomato causes disease in tomato but not in beans. However, such bacteria will elicit a hypersensitive response in beans. Accordingly, in accordance with this embodiment of the present invention, *Pseudomonas syringae* pv. tomato can be applied to bean plants or seeds to impart disease resistance, enhance growth, or control insects without causing disease in that species.

The method of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana, Saintpaulia*, petunia, pelargonium, poinsettia, chrysanthemum, carnation, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solancearum, Pseudomonas syringae* pv. *tabaci*, and *Xanthamonas campestris* pv. *pelargonii*. Plants can be made resistant, inter alia, to the following fungi by use of the method of the present invention: *Fusarium oxysporum* and *Phytophthora infestans.*

With regard to the use of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds, in accordance with the application embodiment of the present invention, the hypersensitive response elicitor protein or polypeptide can be applied by low or high pressure spraying, coating, immersion, or injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart disease resistance to plants, to enhance plant growth, and/or to control insects on the plants.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art.

The vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the R1 plasmid of *A. rhizogenes*. The Ti or R1 plasmid is transmitted to plant cells on infection by *Agrobacterium* and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, and/or control of insects on the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor to impart disease resistance, enhance growth, and/or control insects. Such plants may also be treated with conventional plant treatment agents (e.g., insecticides, fertilizers, etc.).

EXAMPLES

Example 1

Bacterial Strains, Plasmids, and Media

*E. coli* strains were routinely grown in LM (Hanahan, D. (1985) in *DNA Cloning: A Practical Approach*. ed. Glover, D. M. (IRL Press, Oxford), pp. 109– 135, which is hereby incorporated by reference) or Terrific broth (Sambrook, J., Fritsch, E. F., & Maniatis, T. Molecular Cloning, Second Edition. (Cold Spring Harbor Laboratory Press, Cold Spring Harbor, N.Y.), pp. 109–135 (1989)), which is hereby incorporated by reference, at 37° C. The *E. coli* strains primarily used for plasmid constructions were DH5α and DH5aF'IQ (Life Technologies, Grand Island, N.Y.). For standard DNA manipulations, the pBluescript II vectors from Stratagene (La Jolla, Calif.) were used. *P. syringae* pv. tomato DC3000 (Preston, G., *Mol. Plant-Microbe Interact.,* 8:717–32 (1995), which is hereby incorporated by reference) and *P. fluoroscens* 55 (Huang, H. C., *J. Bacteriol.,* 170:4748–56 (1988), which is hereby incorporated by reference) were grown in King's B broth (King, E. O., *J. Lab. Med.,* 22:301–07 (1954), which is hereby incorporated by reference) or in hrp-derepressing fructose minimal medium (Huynh, T. V., *Science,* 245:1374–77 (1989), which is hereby incorporated by reference) at 30° C. Antibiotics were used at the following concentrations (μg/ml): ampicillin, 100; gentamicin, 10; kanamycin, 50; rifampicin, 100; spectinomycin, 50; and tetracycline, 20.

Example 2

DNA Manipulations

DNA manipulations and PCR reactions were performed according to standard protocols (Sambrook, J., Fritsch, E. F., & Maniatis, T. *Molecular Cloning*, Second Edition. (Cold Spring Harbor Laboratory Press, Cold Spring Harbor, N.Y.) (1989); Innis, M. A., Gelfand, D. H., Sninsky, J. J., & White, T. J. *PCR Protocols*. (Academic Press, San Diego) (1990), which are hereby incorporated by reference). Oligonucleotide primers for sequencing or PCR were purchased from Life Technologies. PCR reactions used Pfu polymerase (Stratagene). All DNA sequencing was done at the Cornell Biotechnology Center with an Automated DNA Sequencer, model 373A (Applied Biosystems, Foster City, Calif.). The DNA sequence was analyzed with Genetics Computer Group version 7.3 (Devereaux, J., *Gene,* 12:387–95 (1984), which is hereby incorporated by reference) and DNASTAR (Madison, Wis.) software packages. The DNA sequence of hrpW has been deposited in GenBank under the accession number AF005221.

Example 3

Plant Assays

Tobacco (*Nicotiana tabacum* L. "Xanthi") and tomato (*Lycopersicum esculentum* Mill. "Moneymaker") plants were grown and inoculated with bacteria as described (Gopalan, S., *Plant. Cell,* 8:1095–05 (1996), which is hereby incorporated by reference). For virulence assays, bacterial suspensions containing 10 cells/ml were infiltrated into tomato leaves and monitored daily over a 5-day period for symptom development and bacterial multiplication.

Example 4

Isolation of DNA Flanking the hrp Cluster in *P. Syringae* pv. tomato DC3000

Total DNA from *P. syringae* pv. tomato DC3000 was partially digested with Sau3A, ligated into the BamHI site of cosmid vector pCPP47 (Bauer, D. W., *Mol. Plant-Microbe Interact.,* 10:369–79 (1997), which is hereby incorporated by reference), and packaged into phage particles with the Gigapack III Gold Packaging Extract (Stratagene). About 800 bacterial colonies were transferred to Colony/Plaque Screen Hybridization Membranes (DuPont NEN Research Products, Boston, Mass.) and probed at high stringency with a $^{32}P$-labeled PstI fragment containing hrpR from *P. Syringae* pv. *syringae* 61, which yielded one hybridizing cosmid, pCPP2357. A 6.5 kb EcoRI fragment from pCPP2357 was subcloned into pML123 (Labes, M., *Gene,* 89:37–46 (1990), which is hereby incorporated by reference), producing pCPP2373. pCPP2374 and pCPP2375 were constructed by partially digesting pCPP2373 with MfeI and inserting an EcoRI fragment carrying the $\Omega Sp^r$ fragment from pHP45 Ω into hrpW or transcription unit IV (Prentki, P., *Gene,* 29:303–13 (1984), which is hereby incorporated by reference). A cosmid library was also made in pCPP47 from total DNA from *P. Syringae* pv. *syringae* B728A using the same strategy.

Example 5

DNA Gel Blots

Total DNA (2 μg) was digested with EcoRI and separated by electrophoresis on 0.5% agarose gels. DNA was transferred to Immobilon-N Membrane (Millipore Co. Bedford, Mass.) and hybridized at 62° C. for 8 h in HYB-9 Hybridization Solution (GENTRA Systems, Research Triangle Park, N.C.), with a 1.3 kb PCR-amplified hrpW fragment that was labeled with $^{32}P$ using the Prime-It II kit (Stratagene). The membranes were washed 4 times in 1.0% SDS and 1×SSC followed by 2 washes in 1.0% SDS and 0.2× SSC. Membranes were exposed to OMAT X-ray film for 4 to 12 hr.

Example 6

Preparation of HrpW and Derivatives

The complete coding sequence for HrpW was PCR-amplified from pCPP2368 with the primers 5N-ATGAG- GATCCAGCATCGGCATCACACCC-3N (named W1) (SEQ. ID. No. 3) and 5N-ATGAAAGCTTAAGCTCGGT-GTGTTGGGT-3N (named W2) (SEQ. ID. No. 4) which contained BamHI and HindIII sites, respectively. DNA encoding the N-terminal 186 amino acids of HrpW was PCR-amplified from pCPP2368 using the W1 primer and the primer 5N-ATGAAAGCTTGCCACCGCCTGTTGCAGT-3N (SEQ. ID. No. 5) which contained a HindIII site. DNA encoding the C-terminal 236 amino acids of HrpW was PCR-amplified from pCPP2368 with the primer 5N-AT-GAGGATCCGAGGGTGGCGTAACACCG-3N (SEQ. ID. No. 6) which contained a BamHI site and the W2 primer. Amplified products corresponding to full-length HrpW, the N-terminal and C-terminal portions of HrpW were directionally cloned into the BamHI and HindIII sites of pQE30 (Qiagen) resulting in pCPP2377, pCPP2378, and pCPP2379, respectively. Procedures used to isolate His-tagged proteins using Ni-NTA spin columns (Qiagen) were described (Alfano, J. R., *Mol. Microbiol.,* 19:715–28 (1996), which is hereby incorporated by reference). *E. coli* ABLE K (Stratagene) grown on M9 medium (Sambrook, J., *Molecular Cloning*, Second Edition. (Cold Spring Harbor Laboratory Press, Cold Spring Harbor, N.Y. (1989), which is hereby incorporated by reference), supplemented with glucose (0.2%), casamino acids (0.02%), and thiamine (1 μg/ml), was used to obtain $His_6$-HrpW because of apparent toxicity. SDS-PAGE and immunoblot analyses, using previously obtained anti-HrpZ and anti-HrpW antibodies (He. S. Y., *Cell,* 73:1255–66 (1993); Yuan, J., *J. Bacteriol.,* 178:6399–6402 (1996), which are hereby incorporated by reference) and the Western-Light Chemiluminescent Detection System (Tropix, Bedford, Mass.) and OMAT X-ray film (Kodak, Rochester, N.Y.) were performed as before (Alfano, J. R., et al., *Mol. Microbiol.,* 19:715–28 (1996), which is hereby incorporated by reference).

Example 7

Construction of hrpZ and hrpW Mutations and Marker-Exchange Mutagenesis of *P. syringae* pv. tomato DC3000.

To construct the *P. syringae* pv. tomato DC3000 hrpZ mutation, a 603 bp ClaI fragment internal to hrpZ was deleted from pCPP2334, a LITMUS 28 (new England Biolabs) derivative that contains hrpA and hrpZ, producing pCPP2336. An nptll derivative lacking a transcriptional terminator was PCR-amplified from pCPP2988 (Alfano, J. R., et al., *Mol. Microbiol.,* 19:715–28 (1996), which is hereby incorporated by reference) with primers 5N-CCATC-GATGGTGGTGGCGATAGCTAGACTTGG-3N (SEQ. ID. No. 7) and 5N-CCATCGATGGTCTCGTGATGGCAG-GTTG-3N (SEQ. ID. No. 8) and cloned into the unique Cl aI site of pCPP2336 in the correct orientation. A BglII/HindIII fragment from the resulting construct, pCPP2338, carrying the hrpZ mutation was exchanged for the BglII/HindIII fragment, carried in pCPP2340, producing pCPP2342. A 5.3 kb ecoRI fragment from pCPP2342 that carried the hrpZ mutation was cloned into the broad-host range plasmid, pRK415 (Keen, N. T., et al., *Gene,* 70:191–97 (1988), which is hereby incorporated by reference), producing pCPP2344. An 8.5 EcoRI fragment from pCPP2375 which carried hrpW interrupted with an $\Omega Sp^r$ fragment was subcloned into pRK415 producing pCPP2376. Separately, pCPP2376 and pCPP2344 were electroporated into *P. syringae* pv. tomato DC3000. Loss of the plasmid and retention of the marker was done as previously described (Alfano, J. R., et al., *Mol. Microbiol.,* 19:715–28 (1996), which is hereby incorporated by reference).

Example 8 hrpW Expressed in trans Eliminates the Ability of *P. fluorescens*(pHIR11) to Elicit the HR To identify any hypersensitive response elicitor-like genes in the *P. syringae* pv. tomato DC3000 DNA flanking hrpR, cosmid pCPP2357, which contains this region in vector pCPP47, was isolated. A series of subclones in pML123 were constructed and screened for two potential hypersensitive response elicitor phenotypes: (i) the ability to promote tobacco HR elicitation activity in *P. fluorescens* cells carrying pCPP2274, a ΔhrpZ pHIR11 derivative (Gopalan, S., et al., *Plant Cell.* 8:1095–105 (1996), which is hereby incorporated by reference), and (ii) interference with the HR elicitation activity of *P. fluorescens* cells carrying wild-type pHIR11 (Alfano, J. R., et al., *Mol. Microbiol.,* 19:715–28 (1996), which is hereby incorporated by reference). No subclones had the first phenotype, but one, pCPP2373, had the second. pCPP2373 contains a 6.5-kb EcoRI fragment from pCPP2357 that has transcriptional units IV and V (Lorang, J. M. et al., *Mol. Plant-Microbe Interact.,* 8:49–57 (1995), which is hereby incorporated by reference) and eliminated the HR elicitation activity of *P. fluorescens* (pHIR11) (FIG. 1). To determine which transcriptional unit was responsible for the phenotype, an $\Omega Sp^r$ fragment was inserted into MfeI sites in transcriptional units IV and V to construct pCPP2374 and pCPP2375, respectively. Both plasmids were transformed into *P. fluorescens*(pHIR11) cells, which were then infiltrated into tobacco leaves. Only pCPP2375 blocked HR elicitation (FIG. 1), indicating that transcriptional unit V encoded a protein with one of the characteristics of HrpZ.

Example 9

Figure 2A:
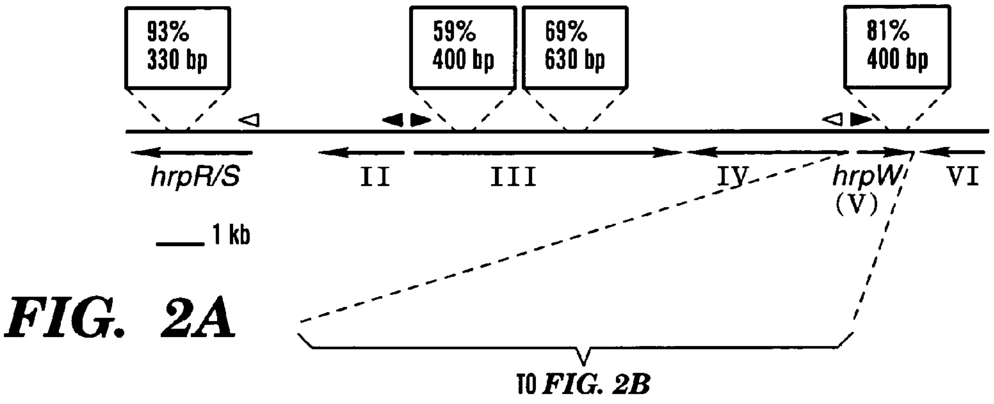
FIGS. 2A–C show a physical map of the *P. syringae* pv. tomato DC3000 hrpW region, its conservation with a corresponding region in *P. syringae* pv. *syringae* B728a, and structural features of HrpW.
Figure 2B:
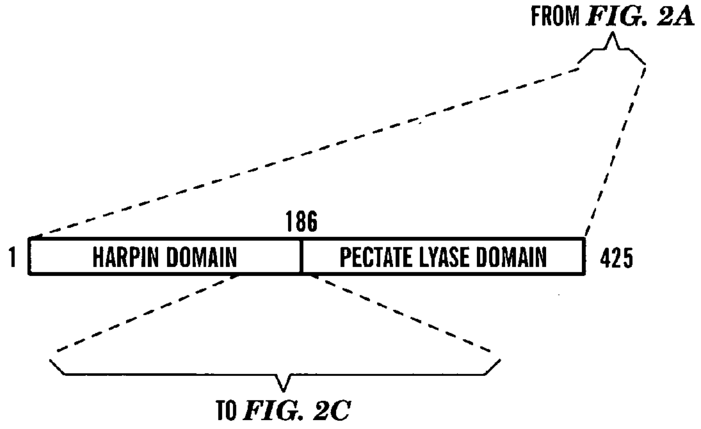
Figure 2C:
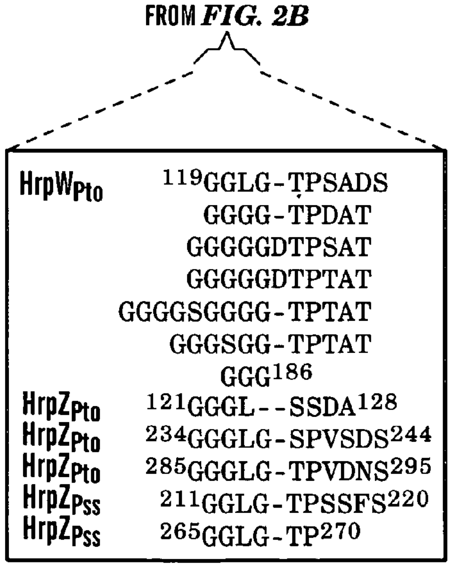

The DNA Sequence of hrpW Predicts a Protein with Both Hypersensitive Response Elicitor and Pel Domains The complete DNA sequence of transcriptional unit V was determined, revealing a 1,275-bp ORF that was designated by hrpW. The gene is preceded by a consensus hrp promoter (Lorang, J. M., et al., *Mol. Plant-Microbe Interact.,* 8:49–57 (1995), which is hereby incorporated by reference), and it is followed by a rho-independent terminator (FIG. 2A). The predicted N-terminal sequence of HrpW matches that of EXP-60, one of the five *P. syringae* pv. tomato DC3000 Hrp-secreted proteins identified by Yuan and He (Yuan, J., et al., *J. Bacteriol.,* 178:6399–402 (1996), which is hereby incorporated by reference). hrpW is flanked by operons transcribed in divergent directions and appears to be in a monocistronic operon. Like hypersensitive response elicitors, the predicted 42.9 kDa HrpW protein is acidic, glycine-rich, lacks cysteine, and is deficient in aromatic amino acids. The predicted protein sequence of HrpW reveals at least two distinct domains (FIG. 2B). A hypersensitive response elicitor-like domain (amino acids 1–186) is rich in glutamine, serine, and glycine. The 119–186 region contains six imperfect glycine-rich repeats with many acidic and polar residues, which align with similar repeats in the HrpZ proteins of *P. syringae* pv. tomato and *P. syringae* pv. *syringae* (FIG. 2C). The T P S/D A T motif in this region is predicted to have ⊕-sheet structure with one side of the β-sheet having all the threonine and serine residues, and the glycine repeats are predicted to be turns by the Garnier-Robson algorithm (Plasterer, T. N., in *Methods in Molecular Biology*, Vol. 70. ed. Swindell, S. R. (Humana Press, Totawa, N.J.), pp. 227–239 (1997), which is hereby incorporated by reference). The alternating P-sheets and turns could form a β-barrel structure. Database searches using BLAST (Altschul, S. F., et al., *J. Mol. Biol.,* 215:403–10 (1990), which is hereby incorporated by reference) revealed no proteins with significant similarity to the hypersensitive response elicitor domain.

In contrast, the C-terminal 236 amino acids of HrpW are similar to several fungal Pels from *Nectria haematococca* mating type IV (*Fusarium solani* f. sp. *pisi*) and to one bacterial Pel from *E. carotovora*. For example, HrpW shows identities of 32.5% with *N. haematococca* PelC (Guo, W., et al., *Arch. Biochem. Biophys.,* 323:352–60 (1995), which is hereby incorporated reference), and 21.2% with Pel-3 from *E. carotovora* (Liu, Y., et al., *Appl. Environ. Microbiol.,* 60:2545–52 (1994), which is hereby incorporated by reference). The amino acid sequence of Pels in this group is dissimilar from the majority of known Pels, and little is known about the active site or tertiary structure of proteins in this group (Henrissat, B., et al., *Plant Physiol.,* 107: 963–76 (1995), which is hereby incorporated by reference).

Example 10 hrpW Appears Widely Distributed in Plant Pathogenic Bacteria and is in a Region Conserved between Two *P. syringae* Pathovars.

Figure 3:
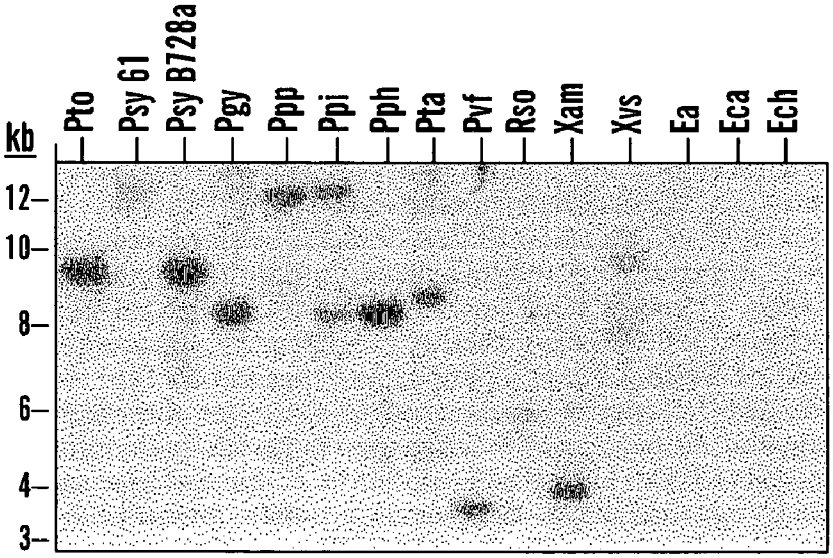
FIG. 3 shows the hybridization of hrpW under high stringency conditions to total DNA from other bacterial plant pathogens. DNA from the indicated pathogens was isolated, digested with EcoRI, resolved on a 0.5% agarose gel, transferred to an Immobilon-N membrane, and hybridized with a $^{32}P$-labeled hrpW subclone at 62° C. Abbreviations: Pto, *P. syringae* pv. tomato; Psy, *P. syringae* pv. *syringae*; Pgy, *P. syringae* pv. *glycinea*; Ppp, *P. syringae* pv. *papulans*; Ppi, *P. syringae* pv. *pisi*; Pph, *P. syringae* pv. *phaseolicola*; Pta, *P. syringae* pv. *tabaci*; Pvf, *P. viridiflava*; Rso, *Ralstonia solanacearum*; Xam, *Xanthomonas campestris* pv. *amoraciae*; Xvs, *X. campestris* pv. *vesicatoria*; Ea, *Erwinia amylovora*; Eca, *E. carotovora*; Ech, *E. chrysanthemi.*

The distribution of hrpW and the conservation of the hrpW region were examined by DNA gel blot and DNA sequence analysis. The hrp W ORF was amplified by PCR and used as a probe for high stringency gel blot hybridization with EcoRI-digested DNA from representative necrogenic Gram-negative plant pathogens (FIG. 3). The hrpW probe hybridized to at least one distinct band for each of the *P. syringae* pathovars tested: *glycinea, papulans, pisi, phaseolicola, tabaci*, and *syringae* strains B728a and 61 (weakly). Hybridization was also observed with *P. viridiflava Ralstonia* (*Pseudomonas*) *solanacearum* (weakly), and *Xanthomonas campestris* pathovars *amoraciae* and *vesicatoria*. No hybridization was observed with DNA from *Erwinia* spp. This region in *P. syringae* pv. *syringae* B728a was further examined by isolating cosmid pCPP2347, which carries DNA hybridizing with both hrpR and hrpW. Restriction mapping and partial DNA sequence analysis indicated that this region is highly conserved in these two *P. syringae* pathovars and that the *P. syringae* pv. *syringae* B728a HrpW also carries a Pel domain (FIG. 2A).

Example 11

Figure 4A:
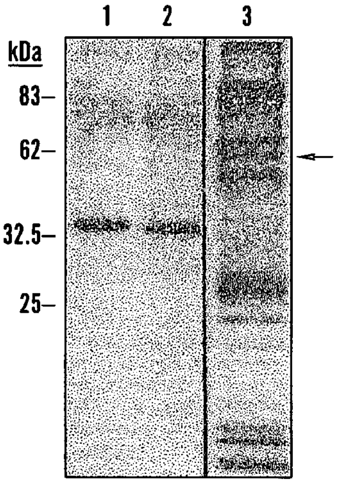
FIGS. 4A–B show SDS-PAGE and immunoblot analysis of preparations containing HrpW and its hypersensitive response elicitor domain and Pel domain fragments.
Figure 4B:
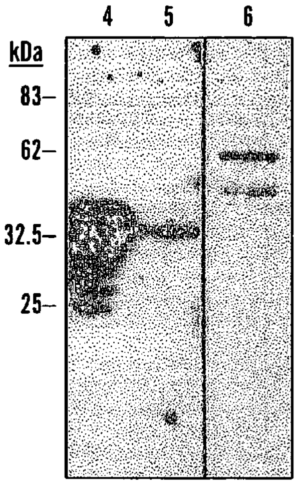
Figure 5A:
FIGS. 5A–F shows the elicitation in tobacco leaves of active tissue death indicative of the HR by cell-free preparations containing HrpW and the N-terminal fragment. The protein preparations analyzed in FIG. 4 were infiltrated into tobacco leaves, in some cases with 1.0 mM Lanthanum chloride. Leaves were photographed 48-hr later.
Figure 5B:
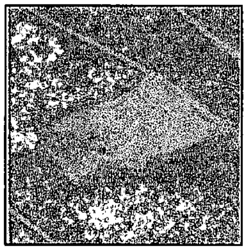
Figure 5C:
Figure 5D:
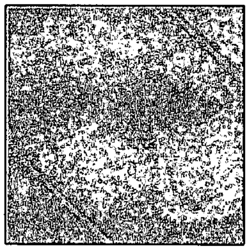
Figure 5E:
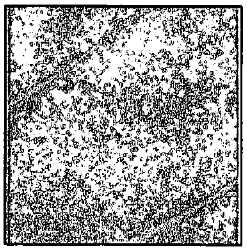
Figure 5F:
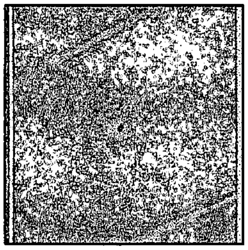

HrpW and its Hypersensitive Response Elicitor Domain Elicit an HR-like Necrosis in Tobacco Leaves, but HrpW and the Pel Domain Lack Detectable Pel activity PCR subclones of hrpW were constructed in pQE30 to permit production of derivatives of HrpW and the two domain fragments carrying N-terminal $His_6$-tags. These fusion proteins were partially purified by Ni-NTA chromatography and analyzed by SDS-PAGE and by immunoblotting with antibodies raised against *P. syringae* pv. tomato DC3000 Hrp-secreted proteins (FIG. 4). Anti-HrpW antibodies did bind to the full-length HrpW and to both fragments, but binding to the hypersensitive response elicitor domain fragment was noticeably weaker. Transformants producing HrpW were highly unstable in their maintenance of the plasmid. Thus, HrpW levels were quite low, and Ni-NTA chromatography yielded a preparation that was only partially enriched in HrpW. Nevertheless, the HrpW preparation elicited a hypersensitive response ("HR")-like necrosis in tobacco leaves, which visibly differed from the necrosis elicited by the *P. syringae* pv. *syringae* 61 HrpZ only in developing ca. 12 hr later (FIGS. 5A–B). The elicitor activity was heat-stable and protease sensitive, and vector control preparations produced no response. The partially purified hypersensitive response elicitor domain fragment also elicited a necrosis that was slightly delayed, and this response, like that elicited by HrpZ, could be inhibited by 1.0 mM lanthanum chloride, a calcium channel blocker (FIGS. 5D–E). Thus, the necrosis elicited by the HrpW harpin domain is an active plant response. In contrast, purified *E. chrysanthemi* PelE, obtained from *E. coli* JA-221 (pPEL748) (Keen, N. T., et al., *J. Bacteriol.,* 168:595–606 (1986), which is hereby incorporated by reference) elicited a black, macerated necrosis that was not inhibited by 1.0 mM lanthanum chloride, 50 μM sodium vanadate, or 100 μM cycloheximide. This is consistent with the expectation that pectic enzymes kill by lysis of turgid protoplasts through weakened cell walls rather than by elicitation of cell death programs. Furthermore, the Pel domain fragment elicited no visible response in the infiltrated tobacco tissue. All three proteins were tested for Pel activity by using the sensitive $A_{230}$ assay for 4,5-unsaturated pectic products (Collmer, A., et al., *Meth. Enzymol.,* 161:329–35 (1988), which is hereby incorporated by reference). No activity was detected despite trying polygalacturonic acid and a 31% methylesterified derivative as substrates, $CaCl_2$ and $MnCl_2$ as cofactors, and several pH levels.

Example 12

The Ability of a *P. syringae* pv. tomato DC3000 hrpZ hrpW Mutant to Elicit the HR is Substantially Reduced Marker-exchange mutagenesis was used to construct *P. syringae* pv. tomato mutants CUCPB5094 (ΔhrpZ::nptII), CUCPB5095 (hrpW::ΩSp$^r$(m abd/cycOB5985*ΔhrpZ::nptII hrpW::ΩSp$^r$). The ΔhrpZ::nptII mutation is functionally nonpolar, and all mutant constructions were confirmed with DNA gel blots and immunoblots. Tobacco leaves were infiltrated with *P. syringae* pv. tomato DC3000 and the three mutant derivatives at two levels of inoculum and then examined 48-hr later for the percentage of infiltrated tissue that was necrotic (Table 1).

TABLE 1

Reduced frequency of hypersensitive response elicitation in tobacco leaves by *P. syringae* pv. Tomato DC30000 hrpZ and hrpW mutants

| *P. syringae* pv. | | Inoculum level (cells/ml) | |
|---|---|---|---|
| tomato strain | Relevant genotype | $1 \times 10^7$ | $5 \times 10^7$ |
| DC3000 | wild type | 17/19[a] | 18/18 |
| CUCPB5094 | ϵhrpZ□nptll | 12/15 | 13/13 |

TABLE 1-continued

Reduced frequency of hypersensitive response elicitation in tobacco leaves by *P. syringae* pv. Tomato DC30000 hrpZ and hrpW mutants

| *P. syringae* pv. | | Inoculum level (cells/ml) | |
|---|---|---|---|
| tomato strain | Relevant genotype | $1 \times 10^7$ | $5 \times 10^7$ |
| CUCPB4096 | hrpW ΩSp$^r$ | 13/15 | 13/13 |
| CUCPB5095 | ϵhrpZ□nptll hrpW ΩSp$^r$ | 7/19 | 15/18 |

[a]The number of inoculated panels showing more than 50% collapse relative to the total number inoculated 48 hr after inoculation.

Only the hrpZ hrpW mutant was significantly reduced in the frequency with which it elicited a robust HR. To determine if this mutant was reduced in virulence, tomato leaves inoculated with the mutant and wild-type DC3000 were monitored for symptom production and bacterial multiplication over a period of 5 days. No difference was observed. To identify an anticipated second hypersensitive response elicitor in *P. syringae*, DNA in the *P. syringae* pv. tomato DC3000 hrp gene region was screened for genes with hypersensitive response elicitor-like phenotypes. hrpW had the expected but paradoxical phenotype of interfering with HR elicitation when expressed in trans and was found to be identical to the previously identified transcriptional unit V and to encode the previously identified Hrp-secreted protein EXP-60 (Lorang, J. M., et al., *Mol. Plant*-Microbe Interact., 8:49–57 (1995); Yuan, J., et al., *J. Bacteriol.,* 178:6399–402 (1996), which are hereby incorporated by reference). Several characteristics of hrpW and its product are relevant to outstanding questions regarding the function of hypersensitive response elicitors, the mechanism by which parasite-promoting "Avr" proteins are transferred through the plant cell wall to the interior of plant cells, and the conservation and organization of virulence loci in plant pathogenic bacteria.

HrpW has several general characteristics of hypersensitive response elicitors, including amino-acid composition, heat-stability, unexpectedly low mobility in SDS-PAGE, and the ability of both full-length and truncated proteins to elicit the HR (Alfano, J. R., et al., *Plant Cell,* 8:1683–98 (1996); He. S. Y., et al., *Cell,* 73:1255–66 (1993); Wei, Z. M., et al., *Science,* 257:85–8 (1992); Alfano, J. R., et al., *Mol. Microbiol.,* 19:715–28 (1996), which are hereby incorporated by reference). HrpW also has 6 glycine-rich repeats that are similar to a repeated sequence found in HrpZ and are reminiscent of the repeat-rich structure of HrpZ (Alfano, J. R., et al., *Mol. Microbiol.,* 19:715–28 (1996), which is hereby incorporated by reference). The general lack of cysteine residues in hypersensitive response elicitors is particularly striking in HrpW, because comparison with the homologous fungal and bacterial Pels reveals that all 6 of the conserved cysteine residues in those proteins have been substituted in HrpW. All of these properties raise the possibility that hypersensitive response elicitors, like the *Salmonella typhimurium* FlgM protein, may be in an infolded state in the absence of its substrate or target (Daughdrill, G. W., et al., *Nature Struct. Biol.,* 4:285–91 (1997), which is hereby incorporated by reference). This appears to be important to FlgM because of spatial constraints on the movement of globular proteins through the flagellum. With hypersensitive response elicitors, an unfolded state is more likely important for penetration into the plant cell wall matrix than for translocation through the Hrp pathway, since several Avr proteins thought to travel the pathway into plant cells are relatively large and cysteine-rich.

The ability of isolated *P. syringae* HrpZ and HrpW proteins to elicit the HR when infiltrated into tobacco leaf tissue may not directly reflect biological function, because the Avr proteins now appear to be both essential and sufficient (once delivered to the plant cytoplasm) for elicitation of the bacterial HR (Alfano, J. R., et al., *Plant Cell,* 8:1683–98 (1996), which is hereby incorporated by reference). Therefore, the hypersensitivity of many plants to hypersensitive response elicitors may be a by-product of the primary activity of these proteins in locally modifying plant cell wall structure in support of parasite-promoting "Avr" protein delivery. Several lines of evidence suggest that the *P. syringae* hypersensitive response elicitors may be such an extracellular component of the Hrp secretion system: (i) hrpZ is located within a hrp secretion operon that appears conserved among *P. syringae* pathovars (Preston, G., et al., *Mol. Plant-Microbe Interact.,* 8:717–32 (1995), which is hereby incorporated by reference), and hrpW (in contrast to typical avr genes) appears to be both conserved and linked to the hrp cluster; (ii) whereas Avr proteins appear to be secreted out of the bacterial cytoplasm only upon contact with the host (analogous to the contact-dependent type III secretion of the *Yersinia* Yop effector proteins (Cornelis, G. R., et al., *Mol. Microbiol.,* 23:861–67) (1997), which is hereby incorporated by reference), HrpZ and HrpW are secreted when the Hrp system is transcriptionally activated, suggesting they may be components of the translocation apparatus; (iii) the finding that the expression in trans of either hrpZ or hrpW inhibits the HR elicitation activity of wild-type bacteria is consistent with hypersensitive response elicitors being components of a stoichiometrically-sensitive protein assembly; (iv) HrpZ associates with the walls rather than the membranes of plant cells, and the protein elicits no response from wall-less protoplasts (Hoyos, M. E., et al., *Mol. Plant-Microbe Interact.,* 9:608–16 (1996), which is hereby incorporated by reference); (v) the presence of a Pel domain in HrpW strongly suggests interaction with the pectic fraction of the cell wall, which is the component controlling porosity of the matrix (Baron-Epel, O., et al., *Planta,* 175:389–95 (1988), which is hereby incorporated by reference). The growing evidence that large Avr proteins, e.g., AvrBs3 (125 kDa) (Van den Ackerveken, et al., *Cell,* 87:1307–16 (1996), which is hereby incorporated by reference), are delivered to the plant cell cytoplasm suggests that the Hrp system can open a channel through the plant cell wall.

The HrpW protein has no detectable Pel activity. Pel homologs with no detectable activity in vitro are also found in the pollen and style tissues of several plants, and the conservation of catalytic residues in these proteins suggests a cryptic enzymatic function (Henrissat, B., et al., *Plant Physiol.,* 107:963–76 (1995), which is hereby incorporated by reference). The lack of detectable Pel activity in HrpW is not surprising given the biotrophic parasitism of *P. syringae* and the damaging effects of typical Pels on plant tissues. However, the conservation of the Pel domains of the *P. syringae* and *E. amylovora* HrpW proteins suggests that these proteins do have a Pel-related function. In contrast, the extreme variation in the elicitor-active domains argues against an enzymatic basis for the elicitor activity of the proteins.

Mutation of transcription unit V did not reduce either the HR or virulence phenotypes of *P. syringae* pv. tomato DC3000 (Lorang, J. M., et al., *Mol. Plant-Microbe Interact.,* 8:49–57 (1995), which is hereby incorporated by reference), and the hrpZ hrpW mutant was significantly reduced only in its HR phenotype (although virulence assay would likely miss a subtle reduction). One interpretation of these observations is that *P. syringae* produces additional hypersensitive response elicitor-like proteins, analogous to the multiple Pel isozymes of *E. chrysanthemi* and *E. carotovora* (Barras, F., et al., *Annu. Rev. Phytopathol.,* 32:201–34 (1994), which is hereby incorporated by reference). Perhaps as a result of host-parasite coevolution or of cell wall structural complexity, redundancy (or subtle specialization) may be characteristic of virulence systems that interact extensively with the plant cell wall.

The presence of sequences hybridizing with hrpW in several other plant pathogenic bacteria, particularly *P. viridiflava* and *X. campestris* is significant for several reasons. Since hrpW does not hybridize with DNA from *E. amylovora* or *E. carotovora*, which are known to produce a similar hypersensitive response elicitor and Pel, respectively, the hybridization with *P. viridiflava* and *X. campestris* suggests that these bacteria produce a protein that is highly similar to HrpW. This, in turn, implies that *P. viridiflava* has a Hrp system and that *X. campestris* produces a hypersensitive response elicitor. Although the Hrp system of *X. campestris* has been extensively characterized (Bonas, U. in "Current Topics in Microbiology and Immunology," Vol. 192: *Bacterial Pathogenesis of Plants and Animals—Molecular and Cellular Mechanisms*. ed. Dangl, J. L. (Springer-Verlag, Berlin), pp. 79–98 (1994), which is hereby incorporated by reference), no hypersensitive response elicitor or any other protein has been found to be secreted by the Hrp system in culture. hrpW should be useful as a probe to clone from *X. campestris* a gene encoding such a protein.

The pathogenicity island concept predicts that the hrp gene cluster is located in a larger region enriched in virulence related genes (Groisman, E. A., et al, *Cell* 87:791–94 (1996); Alfano, J. R., et al., *Plant Cell,* 8:1683–98 (1996), which are hereby incorporated by reference). Some parts of the virulence region would be expected to carry effector-encoding genes that are "switchable" to permit rapid coevolution of the parasite with the host. The hrmAlavrPphE locus at the opposite end of the hrp cluster from hrpR provides such an example. Other, more conserved aregions would carry genes related to essential parasitic functions such as the delivery of effector (e.g., "Avr") proteins to the interior of host cells. Comparison of *P. syringae* pathovars tomato and *syringae* indicates that hrpW is located in such a region. Collectively, these observations suggest a broadly important role for HrpW in bacterial plant pathogenicity. Although both hypersensitive response elicitors and Avr proteins must travel the type III pathway, they differ strikingly in their structural properties, their ability to be secreted in culture, and their effects on host-range determination and other virulence attributes. The discovery of a *P. syringae* hypersensitive response elicitor with a Pel domain provides further evidence that they also differ in their site of action, with many Avr proteins acting inside plant cells and hypersensitive response elicitor acting outside.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated DNA molecule encoding a hypersensitive response eliciting protein or polypeptide, wherein the isolated DNA molecule is selected from the group consisting of (a) a DNA molecule comprising SEQ ID NO: 1, (b) a DNA molecule encoding a protein comprising SEQ ID NO: 2, and (c) a DNA molecule complementary to DNA molecules (a) or (b).

2. The isolated DNA molecule according to claim 1, wherein said DNA molecule is a DNA molecule comprising SEQ ID NO: 1.

3. The isolated DNA molecule according to claim 1, wherein said DNA molecule is a DNA molecule encoding a protein comprising SEQ ID NO: 2.

4. The isolated DNA molecule according to claim 1, wherein said DNA molecule is a DNA molecule complementary to DNA molecules (a) or (b).

5. An expression vector comprising the DNA molecule of claim 1 and a promoter operably coupled to the DNA molecule.

6. The expression vector according to claim 5, wherein the DNA molecule is in sense orientation relative to the promoter.

7. A host cell transformed with the DNA molecule of claim 1.

8. A The host cell according to claim 7, wherein the host cell is a plant cell or a bacterial cell.

9. A The host cell according to claim 7, wherein the DNA molecule is comprised within an expression vector.

* * * * *